US00PP24564P3

(12) United States Plant Patent
Egger

(10) Patent No.: US PP24,564 P3
(45) **Date of Patent: *Jun. 17, 2014**

(54) ***HEUCHERA* PLANT NAMED 'BLONDIE'**

(50) Latin Name: ***Heuchera* sp.**
Varietal Denomination: Blondie

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 144 days.

This patent is subject to a terminal disclaimer.

(21) Appl. No.: 13/507,939

(22) Filed: Aug. 7, 2012

(65) Prior Publication Data

US 2014/0047605 P1 Feb. 13, 2014

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by small red brown spring leaves that mature to a tan color, winter leaves of olive green with red veins, yellow green to creamy yellow flowers in wands with red pedicels, very free flowering on short, red flower stalks, a small, multi-crowned, low mounding habit, and excellent vigor.

1 Drawing Sheet

Botanical denomination: *Heuchera* sp.
Variety designation: 'Blondie'.

BACKGROUND OF THE INVENTION

The present invention relates to a new and distinct cultivar of *Heuchera* and given the cultivar name of 'Blondie'. *Heuchera* is in the family Saxifragaceae. *Heuchera* 'Blondie' originated from a cross between *Heuchera* K266-2, a proprietary non-commercial hybrid, as the seed parent, and *Heuchera* K376-1, a proprietary non-commercial hybrid, as, as the pollen parent.

Compared to the seed parent, *Heuchera* K266-2, the new cultivar is similar, but the leaves of the new cultivar are much smaller.

Compared to the pollen parent, *Heuchera* K376-1, the new cultivar has smaller leaves that are red brown when young to deep green with red veins when mature rather than red purple leaves.

There are no similar *Heuchera* on the market known to the breeder.

This new *Heuchera* is uniquely distinguished by:

1. small red brown spring leaves that mature to a tan color,
2. winter leaves olive green with red veins,
3. yellow green to creamy yellow flowers in wands with red pedicels,
4. very free flowering on short, red flower stalks,
5. small, multi-crowned, low mounding habit, and
6. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a one-year-old plant of *Heuchera* 'Blondie' growing in a one gallon pot in a cold greenhouse in April in Canby, Oreg.

DETAILED PLANT DESCRIPTION

The following is a detailed description of the new *Heuchera* cultivar based on observations of two-year-old specimens growing in one gallon containers in a cold greenhouse in March in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The *Royal Horticultural Society Colour Chart,* 2007 edition.

Plant:

*Form.*—Basal rosette, herbaceous perennial.
*Hardiness.*—USDA Zone 4 to 9.
*Size.*—14 cm tall from top of the foliage to the ground and 30 cm wide.
*Habit.*—Mounding.
*Vigor.*—Excellent.

Leaf:

*Type.*—Simple.
*Arrangement.*—Rosette.
*Shape.*—Broadly ovate to orbicular.
*Number.*—About 40.
*Lobing/division.*—5 to 7 shallow lobes.
*Size.*—4 mm long and 3 mm wide.
*Venation.*—Palmate.
*Margins.*—Crenate.

*Apex.*—Mucronulate.
*Base.*—Cordate.
*Blade size.*—Grows to 7 cm long and 7 cm wide.
*Texture.*—Leathery.
*Surface texture.*—Glandular on top and bottom.
*Petiole description.*—Grows to 11 cm long and 1.5 mm wide, glandular hairs, Greyed Purple 187A.
*Leaf color.*—Color variable, topside, new leaves in spring and summer Greyed Red 178A maturing to Brown 200A then later fading to Yellow Green 148A with lighter veins of Yellow Green 149D, winter leaves Yellow Green 147A with veins Greyed Purple 187A; bottom side between Greyed Purple 187B and N187C.

Inflorescence:
*Size.*—Grows to 4 cm wide and 9 cm long.
*Type.*—Thyrse.
*Number of flowers per thyrse.*—About 100.
*Number of thyrse.*—About 25 in the first spring flush, reblooming all summer.
*Peduncle.*—Grows to 20 cm long, 3 mm wide at base, Greyed Purple 187B, glandular hairs.
*Pedicel.*—Variable in size, with glandular hairs, Greyed Purple 187B.
*Bloom period.*—April through October in Canby, Oreg.

Flower bud:
*Size.*—2 mm wide and 2.5 mm long.
*Description.*—Glandular puberulent, ovoid, down facing.
*Color.*—Yellow Green 1A on top half and Greyed Orange N170B on bottom half.

Flower:
*Type.*—Perfect.
*Shape.*—Campanulate.
*Size.*—4 mm long and 3 mm wide.
*Corolla description.*—5 petals, 2 mm long and 0.5 mm wide, narrowly spatulate, margins entire, tip acute, glabrous top and bottom, White NN155C.
*Calyx description.*—Campanulate, 4 mm long and 3 mm wide, with 5 lobes divided ½ way to the base, each 1.4 mm wide and 2 mm long, glandular hairs outside and glabrous inside, tips obtuse, margin entire; color both sides Yellow Green 145B on top half and Greyed Yellow 160A on bottom half.
*Stamen description.*—5 in number, filaments 2 mm long, White 157D, anthers 0.2 mm, Greyed Orange 177B, pollen none.
*Pistil description.*—1, 2-beaked, 4 mm long and 2 mm wide; Yellow Green 145C overall, ovary 1.5 mm long and 1.5 mm wide; style 2.5 mm long.
*Fragrance.*—None.
*Lastingness.*—Each thyrse blooms for about 3 weeks on the plant.

Fruit:
*Type.*—Two-beaked ovoid capsule.
*Fertility.*—Low.
*Color.*—Greyed Brown 199C.

Seed:
*Shape.*—Linear.
*Size.*—2 mm long.
*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

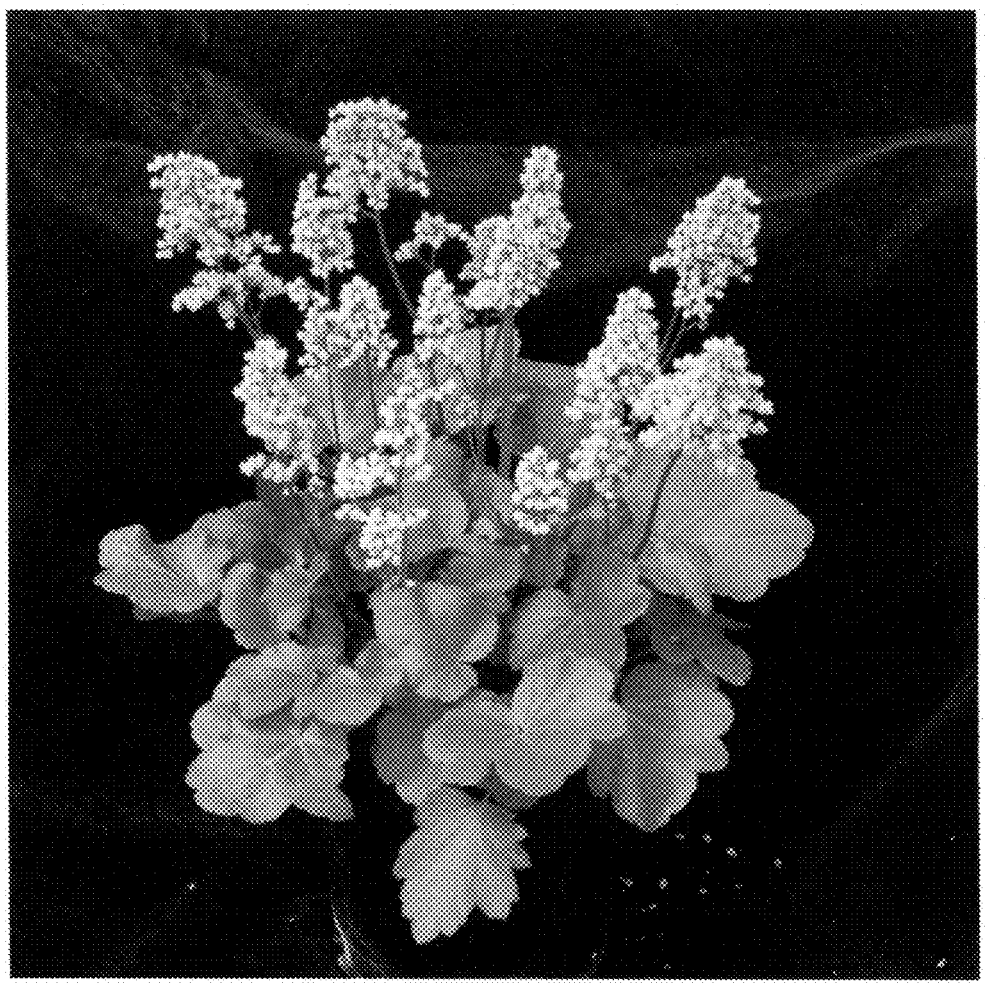

* * * * *